(12) United States Patent
Peterson et al.

(10) Patent No.: US 9,816,973 B2
(45) Date of Patent: Nov. 14, 2017

(54) INDUSTRIAL PROCESS STREAM COMPOSITIONAL HEADSPACE ANALYSIS

(71) Applicants: Nathaniel J. Peterson, Middlebury, VT (US); Yoav Barshad, Brookline, MA (US)

(72) Inventors: Nathaniel J. Peterson, Middlebury, VT (US); Yoav Barshad, Brookline, MA (US)

(73) Assignee: Nova Engineering Ltd., Billerica, MA (US)

( * ) Notice: Subject to any disclaimer, the term of this patent is extended or adjusted under 35 U.S.C. 154(b) by 0 days.

(21) Appl. No.: 14/592,656

(22) Filed: Jan. 8, 2015

(65) Prior Publication Data

US 2015/0192551 A1    Jul. 9, 2015

Related U.S. Application Data

(60) Provisional application No. 61/924,808, filed on Jan. 8, 2014.

(51) Int. Cl.
| | |
|---|---|
| *G01N 30/74* | (2006.01) |
| *G01N 33/00* | (2006.01) |
| *G01N 1/40* | (2006.01) |
| *G01N 21/85* | (2006.01) |
| *G01N 30/12* | (2006.01) |
| *G01N 21/64* | (2006.01) |

(52) U.S. Cl.
CPC ......... *G01N 33/0004* (2013.01); *G01N 1/405* (2013.01); *G01N 1/4055* (2013.01); *G01N 21/85* (2013.01); *G01N 30/12* (2013.01); *G01N 2001/4066* (2013.01); *G01N 2021/6417* (2013.01); *G01N 2021/8578* (2013.01)

(58) Field of Classification Search
CPC ................. G01N 1/2214; G01N 1/405; G01N 2021/6417; G01N 2030/025; G01N 30/482; B01D 15/08
See application file for complete search history.

(56) References Cited

U.S. PATENT DOCUMENTS

| | | | | |
|---|---|---|---|---|
| 3,814,939 | A * | 6/1974 | Parker | G01N 21/64 250/304 |
| 4,384,471 | A * | 5/1983 | Wentzel | G01N 30/08 422/89 |
| 5,290,604 | A * | 3/1994 | Nielsen | B05D 1/025 118/300 |
| 5,392,634 | A * | 2/1995 | Asano | G01N 30/40 422/89 |

(Continued)

*Primary Examiner* — Natalie Huls
(74) *Attorney, Agent, or Firm* — Davis, Malm & D'Agostine, P.C.

(57) ABSTRACT

A system and method for compositional analysis of a process stream in an industrial process transports a liquid process stream through an absorption/desorption packed column (A/D column), along with a carrier gas. A gas phase combination of the carrier gas and one or more solutes from the liquid process stream is passed out of the A/D column to a flow cell for analysis by an analyzer to determine presence and concentration of the one or more solutes within the gas phase. A processor uses the concentration of the solutes within the gas phase to perform a headspace analysis to determine the concentration of the solutes in the process stream.

30 Claims, 2 Drawing Sheets

(56) References Cited

U.S. PATENT DOCUMENTS

| | | | | |
|---|---|---|---|---|
| 5,536,301 A * | 7/1996 | Lansbarkis | ............ | B01D 53/02 95/117 |
| 5,693,538 A * | 12/1997 | Capuano | ................ | G01N 30/06 422/83 |
| 5,827,353 A * | 10/1998 | O'Neil | .................... | G01N 30/08 95/87 |
| 5,949,536 A * | 9/1999 | Mark | ...................... | G01N 21/05 250/428 |
| 6,112,602 A * | 9/2000 | Mitra | ...................... | G01N 30/00 73/863.12 |
| 2011/0111509 A1* | 5/2011 | Trygstad | .............. | G01N 21/359 436/55 |
| 2012/0103185 A1* | 5/2012 | Vaidya | ................... | B01D 53/14 95/11 |
| 2014/0192343 A1* | 7/2014 | Harrison | ................... | G01J 3/02 356/51 |
| 2014/0345370 A1* | 11/2014 | Marotta | ................ | G01N 30/88 73/61.55 |
| 2015/0068280 A1* | 3/2015 | Ricoul | ................... | G01N 1/405 73/23.41 |
| 2015/0151240 A1* | 6/2015 | Laroche | ............ | B01D 53/1468 423/210 |
| 2015/0226629 A1* | 8/2015 | Murthy | ................... | G01M 3/20 73/40.7 |

* cited by examiner

INDUSTRIAL PROCESS STREAM COMPOSITIONAL HEADSPACE ANALYSIS

RELATED APPLICATION

This application claims the benefit of U.S. Provisional Patent Application Ser. No. 61/924,808, entitled Headspace Column, filed on Jan. 8, 2014, the contents of which are incorporated herein by reference in their entirety for all purposes.

BACKGROUND

Technical Field

This invention relates to industrial process stream compositional analysis, and more particularly to an online system for process stream compositional analysis using a headspace column to separate materials of interest from the process stream for analysis.

Background Information

The operations of process plants have been leveraged by the availability of analytical methods, for example, through the use of laboratory measurements or online analyzers. These types of results are valued by plant operations because they are typically regarded as reliable. For example, with respect to hydrocarbon and/or refining operations, primary analytical test methods provide a critical basis for custody transfer of products whose properties have been ascertained in accordance with industry standard test methods such as those developed and promulgated by ASTM International.

Notwithstanding the importance of these primary test methods, they do suffer from certain inadequacies. For example, laboratory measurements typically may be available only once or several times per day. Furthermore, several hours can elapse between the obtaining of a discrete sample and the reporting of results from tests performed on it, severely limiting the possibility to control the process on the basis of those results. Additionally, sample stability, sample contamination, issues of representative sampling, and uncertainty associated with the execution of test procedures may result in erroneous ample values being returned.

Improving the availability, integrity, and reproducibility of test data has in many cases motivated the on-line deployment of measurements. However, depending upon the type of measurement and analysis being performed, the measurement of some liquids, such as hydrocarbon streams, wastewater, and other multi-component process streams, using conventional photometric or spectrometric devices, has been problematic. These liquids, for example, may be too optically dense for the analyzer to get adequate light through the sample. They may also coat the lenses of the analyzer, which tends to decrease analyzer accuracy and increase maintenance time. These liquids may also have unknown irregular background absorption in the spectral region of the particular materials of interest, to further decrease accuracy of readings. Still further, these liquids may contain particulates which block light across the analytical spectrum to create artificially high concentration readings. Liquids may also include air bubbles, which refract the light and scatter it creating artificially high concentration readings. Non-volatile components may also absorb in the spectral region being analyzed, which may be particularly problematic in wastewater analysis.

Even small deviations in measurement accuracy can significantly impact the economies of production for large scale processes similar to those process units found in petroleum refineries and petrochemical plants. There remains a need in the art for improved methods of measuring properties of industrial process streams, such as hydrocarbon streams and other dirty or multi-component streams, preferably on-line in substantially real-time. Furthermore, there remains a need in the art for improved methods of measuring properties of hydrocarbon streams with a high degree of accuracy.

SUMMARY

In one aspect of the invention, a system is provided for compositional analysis of a process stream in an industrial process. The system includes a fluid flow conduit extending in a downstream direction from a liquid inlet to a liquid outlet, configured to transport a liquid phase of the process stream therethrough. The fluid flow conduit includes an absorption/desorption packed column (A/D column) in fluid communication between the liquid inlet and the liquid outlet, the A/D column configured to transport the liquid phase in the downstream direction therethrough. A gas inlet and a gas outlet are used to transport gas into and out of the A/D column. Packing materials within the A/D column are configured to disrupt flow of the liquid phase through the A/D column and to promote contact with a carrier gas supplied to the gas inlet, so that a gas phase combination of the carrier gas and one or more solutes from the liquid phase passes through the gas outlet. A flow cell communicably coupled to the gas outlet, is configured to transport the gas phase therethrough. A chemical analyzer captures response to analysis of the gas in the flow cell and uses the captured response to determine presence and concentration of the one or more solutes within the gas phase. A processor uses the concentration of the solutes within the gas phase to perform a headspace analysis to determine the concentration of the solutes in the process stream.

Another aspect of the invention includes a method for compositional analysis of a process stream in an industrial process. The method includes transporting a liquid phase of a process stream through a fluid flow conduit that includes an absorption/desorption packed column (A/D column), and transporting a carrier gas into the A/D column through a gas inlet to contact the liquid phase. A gas phase combination of the carrier gas and one or more solutes from the liquid phase is captured as it exits the A/D column through the gas outlet, and transported to a flow cell. A chemical analyzer captures response to analysis of the gas phase in the flow cell to determine presence and concentration of the one or more solutes within the gas phase. A processor uses the concentration of the one or more solutes within the gas phase to perform a headspace analysis to determine the concentration of the one or more solutes in the process stream.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Figure 1:
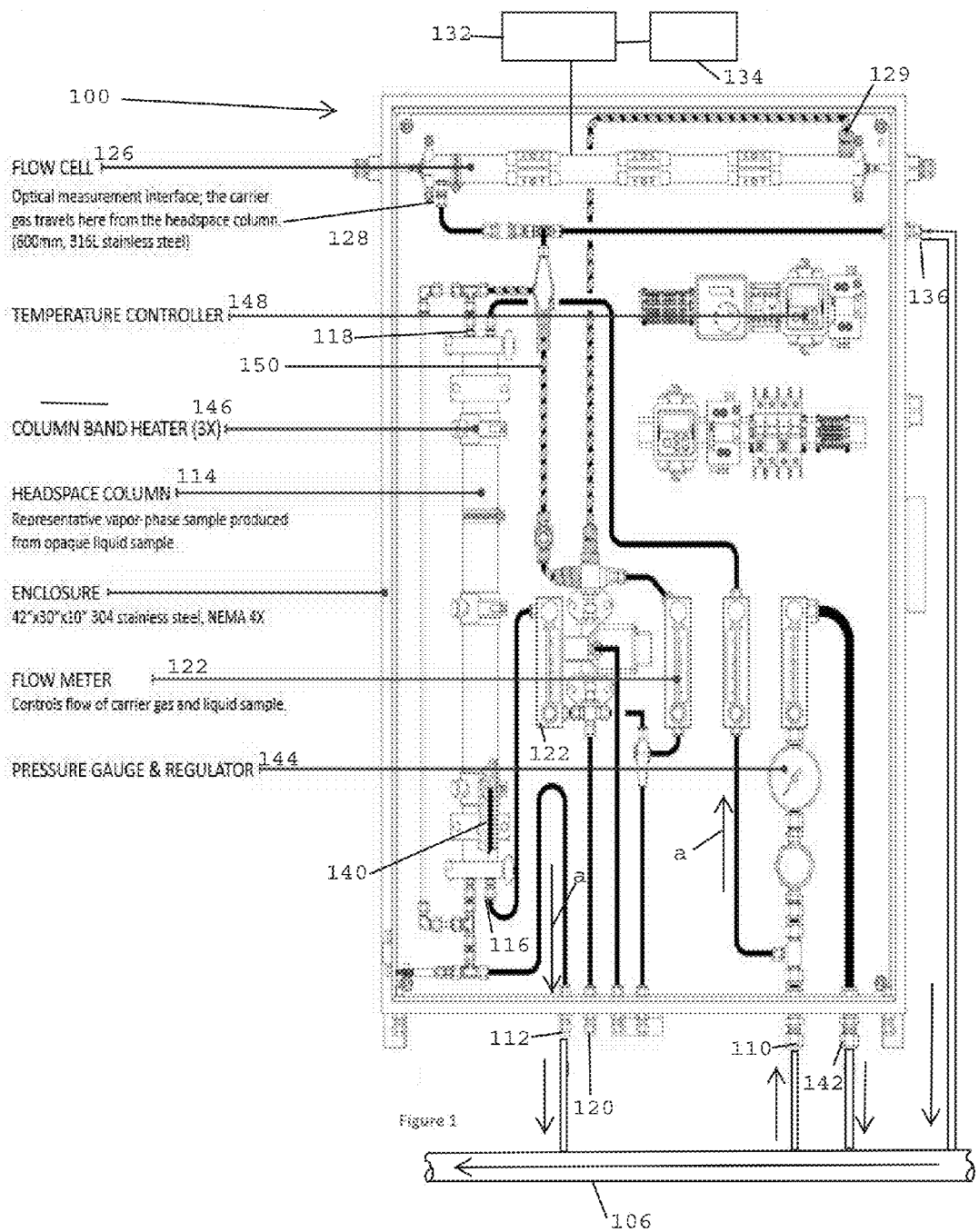
FIG. 1 is an elevational view of aspects of an embodiment of a process stream analysis system of the present invention.

In the following detailed description, reference is made to the accompanying drawings that form a part hereof, and in which is shown by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. In addition, well-known structures, circuits and techniques have not been shown in detail in order not to obscure the understanding of this description. The following detailed description is, therefore, not to be taken in a limiting sense, and the scope of the present invention is defined by the appended claims and their equivalents.

As used in the specification and in the appended claims, the singular forms "a", "an", and "the" include plural referents unless the context clearly indicates otherwise. For example, reference to "an analyzer" includes a plurality of such analyzers. In another example, reference to "an analysis" includes a plurality of such analyses.

Although specific terms are employed herein, they are used in a generic and descriptive sense only and not for purposes of limitation. All terms, including technical and scientific terms, as used herein, have the same meaning as commonly understood by one of ordinary skill in the art to which this invention belongs unless a term has been otherwise defined. It will be further understood that terms, such as those defined in commonly used dictionaries, should be interpreted as having a meaning as commonly understood by a person having ordinary skill in the art to which this invention belongs. It will be further understood that terms, such as those defined in commonly used dictionaries, should be interpreted as having a meaning that is consistent with their meaning in the context of the relevant art and the present disclosure. Such commonly used terms will not be interpreted in an idealized or overly formal sense unless the disclosure herein expressly so defines otherwise. Where used in this disclosure, the term "real-time" refers to sensing and responding to external events nearly simultaneously (e.g., within milliseconds or microseconds) with their occurrence, or without intentional delay, given the processing limitations of the system and the time required to accurately respond to the inputs.

An aspect of the present invention was the recognition that in many prior applications, measurements were taken from samples directly. For example in an application looking at Hydrogen Sulfide dissolved in water, radiation (e.g., light) from an analyzer would be shown directly through the liquid sample and the content could easily be analyzed. The amount of light on a clean water sample was compared to the amount of light on the process sample. This permitted one to determine the absorption curve, which could be correlated to the amount of $H_2S$ in the stream. It was recognized, however, that many other compounds show up in the ultraviolet spectrum, which tend to interfere with the reading of the $H_2S$. In particular, metal ions and aromatics can absorb in the UV region and make it difficult to measure the $H_2S$. In addition, particulates in the stream along with air bubbles in the stream block out more light and make it difficult to analyze the absorbance of the $H_2S$. Thus, while reasonably accurate measurements may be made in relatively clear liquid, this is rarely the case in many applications. For example, it is often desirable to measure $H_2S$ in crude oil. However, there is currently no direct analysis that can be done with UV/VIS (Ultra Violet and Visible spectrum spectroscopy) analyzers because sufficient light typically cannot get through the sample to determine absorbance values. The inventors recognized that it would be advantageous to separate the $H_2S$ from the liquid phase and bring it to the vapor phase to decrease the effects of the background compounds and to be able to get light through the sample.

Another aspect of the invention was the inventors' recognition that devices such as spargers have long been used to sample headspace over a liquid to infer information about the content of the liquid. They also recognized that conventional absorption desorption columns (A/D columns) are commonly used in chemical plants to effect mass transfer from gas to liquid and from liquid to gas in steady state (i.e., continuous) operation. The relatively large surface area provided by these A/D columns, when used with controlled flow rates therethrough, provides an accurate and well understood interface for liquid/gas mass transfer. These A/D columns are typically used in to scrub contaminants, such as $CO_2$, from gas flows by trapping them in liquid flows.

Embodiments of the present invention leverage the capabilities of an A/D column, but instead of trapping gas flows in liquid flows such as in scrubbing operations, the A/D column is used to liberate materials from liquid flows as gas flows. The gas flows are then sent to an on-line analyzer, where the gas flow is analyzed and used to infer the concentration of materials in the original liquid flow. This use of an A/D column along with a carrier gas to create headspace gas for analysis in a continuous manner has been found to provide relatively rapid response time and strong correlation between gas and liquid phase. Moreover, this approach for bringing volatile compounds (solutes) out of the liquid process stream in the gas phase and then using that gas phase to infer the concentration of the solute in the liquid by headspace analysis in a continuous (on-line) manner is believed to be a unique and innovative.

Absorption, also known as scrubbing, involves contact between gas and liquid phase materials. Gas absorption is a unit operation (mass transfer operation) in which one or more species (solute) is removed from a gaseous stream by dissolution in a liquid (solvent). The insoluble component(s) present in the gas stream not absorbed is generally referred to as carrier gas. At least two methods of operation in gas absorption may be used, namely, counter-current and co-current operations. Co-current absorption tends to be less efficient than counter-current operation in some applications. For counter-current operation, the gas which leaves the column or tower via the top enters from below while the liquid flows in through the top and exits via the bottom in an opposite direction.

Absorption may be reversed by sending the (e.g., $CO_2$-rich) absorbent to a desorber (stripper). Desorption involves the removal of a solute component from a liquid stream into a gas stream when in contact with an inert carrier gas (or steam, air, etc.). The solute is thus desorbed from the liquid in the gas phase along with the inert gas. The skilled artisan will recognize that factors such temperature, pressure, and flow rate of the liquid and gas phases may be determined based on the particular materials present within the process flow, for operational efficiency.

Packed columns may be employed as desorbers, with the packing functioning as contactors which provide a relatively large area of contact between the liquid and the gas phase. In particular embodiments, the contactors operate by spreading the liquid into thin films that flow through a continuous gas phase. In other embodiments, contactors may operate by dividing the gas into small bubbles in a continuous liquid phase (e.g., bubble cap trays), and/or by forming the liquid into small drops in a continuous gas phase (e.g., spray chambers). The packing elements (contactors) may be dumped, i.e., random packing, or structured, i.e., non-random packing. While the former is predominantly used, the later may be used in some applications. Stacked packing may also be used in some applications. Dumped column packing may take the form of steel or aluminum rings, but often includes inexpensive, inert materials such as plastics, typically of 6 to 75 mm in dimension (e.g., diameter). Stacked packing units are typically of 50 to 200 mm in diameter. Typical dumped packing used in packed columns include Raschig rings, Lessing rings, berl saddles, intalox saddles, tellerettes and pall rings.

Figure 2:
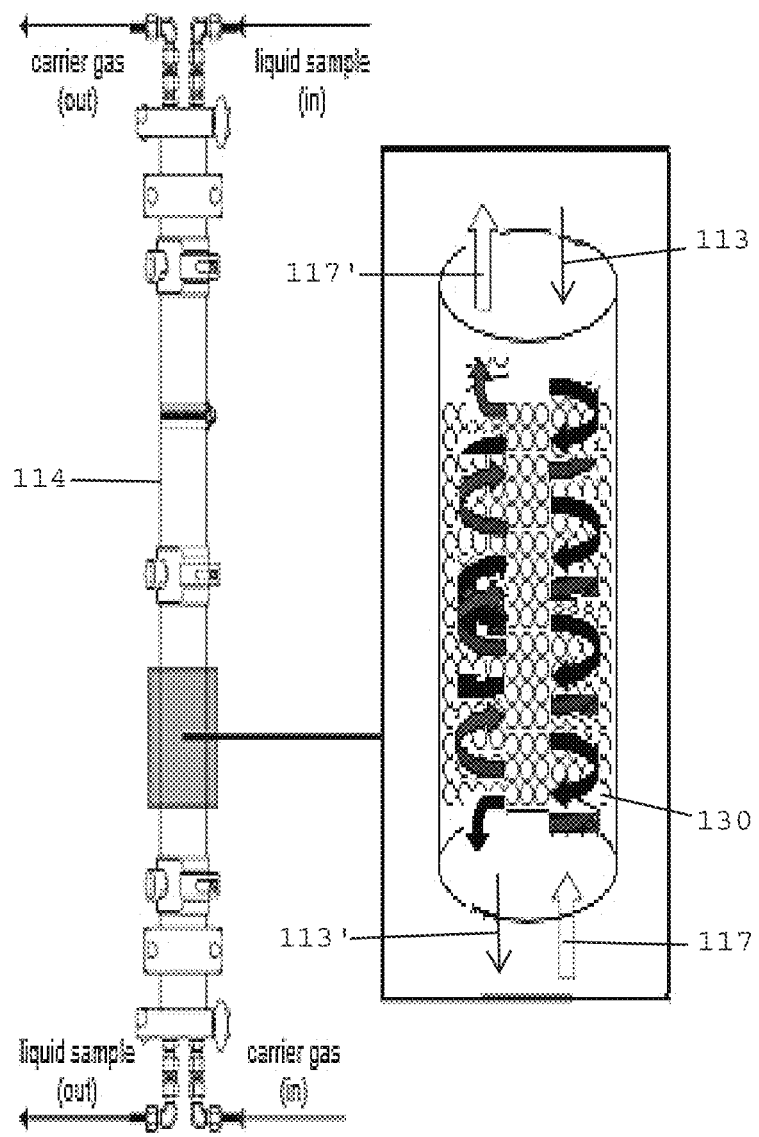
FIG. 2 is an elevational view, on an enlarged scale, of a component of FIG. 1, with a portion thereof expanded and shown schematically to illustrate operation thereof.

Referring now to the figures, various embodiments of the present invention will be more thoroughly described. Turning now to FIG. 1, an embodiment of an analysis system 100 in accordance with the present invention provides compositional analysis of a process stream 106 in an industrial process. System 100 includes a fluid flow conduit extending in a downstream direction, shown by arrows a, from a liquid (e.g., process stream) inlet 110 to a liquid outlet 112, to transport a liquid phase of the process stream therethrough. As shown, liquid inlet 110 is configured for receiving process fluid from process 106, and liquid outlet 112 is configured to return process fluid to process 106. As also shown, the fluid flow conduit of system 100 includes an absorption/desorption packed column (A/D column) 114 in fluid communication between the liquid inlet 110 and liquid outlet 112, configured to transport the liquid phase 113 (FIG. 2) of the process stream in the downstream direction therethrough. The A/D column 114 also has a gas inlet 116 and a gas outlet 118, configured to transport gas into and out of the A/D column. In particular embodiments, the A/D column is a counter-flow column, in which the gas flows in a direction opposite, e.g., upstream, to that of the liquid phase, such as shown at 117 (FIG. 2). In the embodiment shown, the gas inlet 116 is supplied with a carrier (e.g., "zero") gas via carrier supply port 120 and a flowmeter 122. Gas emerging from the gas outlet 118 is supplied to a flow cell (e.g., an optical measurement interface or analyzer sampling unit) 126, as discussed hereinbelow. The A/D column 114 includes packing materials 130 (FIG. 2) disposed therein, the packing materials configured to disrupt flow of the liquid phase 113 through the A/D column 114 and to promote contact with the carrier gas supplied to the gas inlet 116. The particular packing materials used may vary depending on the application, and may include any of the types described hereinabove. In particular embodiments, the packing material may be removable, to facilitate replacement with different types of packing material optimized for different application. In addition, more than one type of packing material may be used within a single A/D column.

This contact within the A/D column 114 serves to effect mass transfer of materials of interest, such as volatile solutes within the liquid, from the liquid phase 113 to a gas phase, so that the gas phase 117' emerging from the A/D column 114 at gas outlet 118 includes a combination of the carrier gas and one or more solutes removed from the liquid process stream 113. The liquid phase 113' emerging from the A/D column 114 thus has a commensurately reduced concentration of the solute(s).

As mentioned above, a flow cell 126 is disposed in fluid communication with the gas outlet 118, so that the gas phase emerging from the A/D column 114 flows into the flow cell 126 via sample inlet 128, and exits the flow cell via sample outlet 129. An analyzer 132, e.g., a radiative analyzer such as the NOVA II™ UV-Vis/SW-NIR Spectrophotometer commercially available from Applied Analytics, Inc. (New York, N.Y.), is operatively engaged with the flow cell 126, to apply radiation to the gas phase within the flow cell 126, and to capture responsive radiation passing through, or otherwise emanating from, the gas phase 117. Although spectrometers or other radiative analyzers such as fluorometers or spectrofluorometers may be preferred in many applications, it should be recognized that substantially any other type of chemical analyzers, including, for example, gas chomatographs (GCs), may be used without departing from the scope of the invention. The analyzer 132 then uses the captured responsive radiation in a conventional manner to determine presence and concentration of the one or more solutes within the gas phase 117. A processor 134, communicably coupled to the analyzer 132, is configured to use the determined concentration of the solute(s) within the gas phase to perform a headspace analysis to infer the concentration of the one or more solutes in the process stream 113 entering the A/D column 114. This headspace analysis may effected in a conventional manner, e.g., using a proportionality constant determined experimentally based on lab testing of similar process fluid, to determine the actual concentration of the solute(s) within the process fluid.

As also shown, in particular embodiments, after being analyzed the gas phase exiting flow cell 126 at sample outlet 129 is returned to the process 106 via gas outlet 136. Since the gas phase now includes the carrier gas, in some embodiments, the carrier gas is simply returned to the process 106 along with the solute(s) in the gas phase. However, in embodiments in which the addition of the carrier gas to the process is undesirable, the carrier gas may be removed from the gas phase prior to returning the gas phase to the process. This removal may be accomplished in any convenient manner known to those skilled in the art. For example, depending on the particular application, the gas phase may be cooled to condense out the solute(s), leaving the carrier gas in its gaseous state. The condensed solute(s) may then be returned to the process, and the carrier gas collected or vented. Additionally, in cases where the gas phase is not desired the gas may be vented to the atmosphere and a scrubber or flare may be used to ensure safe emissions. Alternative approaches include gas stripping operations such as discussed hereinabove.

This return to process 106 of the solute(s) from the gas phase via outlet 136 or the venting of the gas phase, along with the return of the liquid phase via liquid outlet 112, enables system 100 to function in an on-line manner, to facilitate analysis of the process stream 106 in real time without having to stop the process and/or perform analysis off line, such as by withdrawing a sample and sending it to a lab for analysis.

In particular embodiments, the carrier gas includes an inert gas such as nitrogen. Other gases useful as carrier gases may include air or steam, etc. Moreover, in some embodiments it may be desirable to supply the carrier gas through tubing that passes partially through the A/D column 114, such as shown in a broken-away portion of FIG. 1 at 140.

While not required in some embodiments, this use of internal tubing may be used to release the carrier gas deeply within the packing 130 (FIG. 2) to help facilitate interaction with the liquid.

Those skilled in the art will recognize that in many applications, it may be desirable to monitor and maintain the height of the process liquid within the A/D column 126 at optimal levels. This level monitoring may be accomplished by any number of conventional level indicators, ranging from conventional float valves to optical sensors, etc., e.g., including pressure traps configured to release liquid through a drain 142. In the embodiment shown, drain 142 is configured to return the liquid to process 106 once a predetermined pressure is reached within the system, such as determined by pressure gauge and regulator 144. Other optional features usable with system 100 include one or more heaters and temperature controllers to control the heat at various points within the fluid flow conduit and/or gas flow path of system 100. In the exemplary embodiment of FIG. 1, band heaters 146, communicably coupled to a temperature controller 148, are used to control the temperature of A/D column 114. The controller 148 may also be used to control resistive heaters 150 wrapped around portions of the gas flow path to and from the flow cell 126, to help prevent the gas phase 117' from condensing. Moreover, although a flow meter 122 was shown and described for measuring the flow of the carrier gas, those skilled in the art will recognize that any number of additional flowmeters 122 may be used to control the flow rates of others of the various fluid flows. For example, as shown, flow meters may be used to monitor and/or control the flow rate of the liquid phase entering system 100 through liquid inlet 110, the liquid phase exiting the system through drain 142, and the supply of any span gas typically used to calibrate the system. The temperature, pressure, and flow of the fluids through the system may thus be controlled to optimize operation based on the process fluid, the solute(s) of interest, and carrier gases associated with particular applications.

This separation of the solute(s) from the liquid process stream effectively removes non-volatile compounds, i.e., the optically dense materials in the liquid, from the measurement medium to simplify analysis by sending a radiation-permeable gas to the analyzer. The bubbles, particulates, and non-volatile components are left in the liquid phase, so that the components in the gas phase can be easily measured. Moreover, by temperature controlling the column, the system 100 can be optimized to control which components come out of the liquid phase for analysis.

Particular embodiments are configured to maintain gas flow rates within a range of about 75 to 200 cc/min, with a range of about 100 to 150 cc/min preferred for some applications. These embodiments are also configured to maintain liquid flow rates within a range of about 200-800 ml/min, with 300-500 ml/min preferred for some applications. Pressures in these embodiments are maintained within a range of about 5 to 50 psi, with a range of about 10 to 35 psi preferred in some applications. Temperatures in the system are maintained within a range of about 35 to 75 degrees C., with a range of about 45 to 65 degrees C. preferred for particular applications. The temperatures, pressures, and flow rates are subject to the needs of particular applications. For example, in an application involving the $H_2S$ in water, the gas flow rate is maintained at about 100 cc/min, while the liquid flow rate is maintained at about 400 ml/min. Pressure in the column is maintained at about 15 psi, with pressure at the liquid inlet to the column maintained at 30 psi, and pressure at the gas inlet 116 maintained at 30 psi. The column is held at about 50 degrees C. and the flow cell 126 is held at about 60 degrees C.

Having described various embodiments and optional features for a system of the present invention, the following is a description of operation thereof, which is applicable to various applications, including determination of the concentration of $H_2S$ in crude oil, Ammonia and $H_2S$ in dirty waste water, and $H_2S$ and $CO_2$ in Rich Amine Solution.

For example, when measuring the concentration of $H_2S$ in crude oil, the process fluid, in this case the crude oil, flows up through liquid input 110 and enters the top of the column 114 while the carrier gas, in this case nitrogen or air, flows into the bottom of column 114 through the gas inlet 116 and carrier supply port 120. The gas and the liquid contact each other in the column packing as shown and described with respect to FIG. 2. Liquid sample comes to equilibrium with the gas sample, and some of the solutes (volatile liquids and/or gas dissolved in the liquid), in this case $H_2S$, absorb into the nitrogen stream. As used herein, "equilibrium" refers to a mass balance equilibrium through the column in which flow rates, temperature, and pressure within the column are kept constant, so that a constant volume of the $H_2S$ is pulled out of the liquid into the vapor phase. Once this equilibrium is achieved, the gas phase 117' is analyzed in the flow cell 126 by the analyzer (e.g., spectrophotometer) 132. The processor 134 is then used to back calculate the concentration of the solute in the liquid 113 from the concentrations in the vapor phase, using the proportionality constant that was calculated experimentally.

It is noted that at equilibrium, the concentration of the solute (e.g., volatile components) in the gas is directly proportional to the concentration of the solute in the liquid phase. This equilibrium is governed by the aforementioned proportionality constant. The constant is determined experimentally by taking the gas concentration determined by the analyzer and comparing it to a laboratory determined concentration for the liquid. A sample of the process liquid is thus typically analyzed in a lab at the beginning of a sample run through system 100, in order to determine the actual ratio of the solute in the sample. Once determined, this actual ratio is compared to the concentrations determined by analyzer 132 to generate the proportionality constant. The proportionality constant is then used by processor 134 during subsequent on-line analysis to convert the vapor concentrations back to the liquid concentrations.

In the preceding specification, the invention has been described with reference to specific exemplary embodiments for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

It should be further understood that any of the features described with respect to one of the embodiments described herein may be similarly applied to any of the other embodiments described herein without departing from the scope of the present invention.

The following illustrative example demonstrates certain aspects and embodiments of the present invention, and is not intended to limit the present invention to any one particular embodiment or set of features.

EXAMPLE

A system substantially as shown and described with respect to FIG. 1 was used to read 0-300 ppm $NH_3$ in water at a melamine production plant. When the sample was taken off the process stream it was at 60 degrees C., and filtered through a tornado filter to remove particulates. The liquid sample was flow regulated using a rotameter to 300 cc/min and sent to a 12 inch by 2½ inch diameter column 114 packed with ⅝ inch stainless steel Pall rings. Instrument air was used as the carrier gas, and flowed through the column from the bottom in a counter-flow arrangement to bring $NH_3$ from the liquid into gas (vapor) phase, with the gas flow rate regulated to 200 ml/min using a rotameter. The column 114 and flow cell 126 were both maintained at 70 degrees C., which kept the vapor from condensing in the flow cell, and kept the fraction of the $NH_3$ constant. The gas phase was analyzed by NOVA II™ UV-Vis/SW-NIR Spectrophotometer (Applied Analytics, Inc., New York, N.Y.) and a concentration was able to be obtained and accurately correlated back to the actual liquid concentration using a factor as determined by lab testing.

Having thus described the invention, what is claimed is:

1. A system for compositional analysis of a process stream in an industrial process, the system comprising:
    a fluid flow conduit extending in a downstream direction from a liquid inlet to a liquid outlet, configured to continuously transport, without trapping, a liquid phase of the process stream therethrough;
    the fluid flow conduit including a chemically inert packed column (A/D column) in fluid communication between the liquid inlet and the liquid outlet, the A/D column configured to continuously transport the liquid phase in the downstream direction therethrough;
    the A/D column having a gas inlet and a gas outlet, configured to transport gas into and out of the A/D column;
    the A/D column including chemically inert packing materials disposed therein, the packing materials configured to disrupt flow of the liquid phase through the A/D column and to promote contact with a carrier gas supplied to the gas inlet, to achieve mass transfer with the liquid phase to create a phase equilibrium between the liquid phase and the carrier gas wherein a gas phase combination of the carrier gas and one or more solutes from the liquid phase continuously passes through the gas outlet;
    a flow cell communicably coupled to the gas outlet, the flow cell configured to transport the gas phase therethrough;
    a chemical analyzer operatively engaged with the flow cell, the analyzer configured to capture response to analysis of the one or more solutes, and to use the captured response to determine presence and concentration of the one or more solutes within the gas phase; and
    a processor communicably coupled to the analyzer, the processor configured to use the concentration of the one or more solutes within the gas phase to perform a headspace analysis to determine the concentration of the one or more solutes in the process stream.

2. The system of claim 1, wherein the chemical analyzer comprises a radiative analyzer operatively engaged with the flow cell, the radiative analyzer configured to apply radiation to the gas phase in the flow cell, to capture responsive radiation from the flow cell, and to use the captured responsive radiation to determine presence and concentration of the one or more solutes within the gas phase.

3. The system of claim 2, wherein the radiative analyzer comprises one or more spectrometers.

4. The system of claim 1, wherein the gas inlet and gas outlet respectively comprise a counterflow inlet and a counterflow outlet configured to transport the carrier gas in the upstream direction through the A/D column.

5. The system of claim 1, wherein the carrier gas comprises an inert gas.

6. The system of claim 1, wherein the carrier gas flows at least partially through the A/D column in tubing.

7. The system of claim 1, wherein height of the process fluid height in the column is monitored with level indicator.

8. The system of claim 6, wherein the process fluid level is maintained though a pressure trap.

9. The system of claim 1, wherein portions of the system are temperature controlled.

10. The system of claim 1 wherein the column is temperature controlled.

11. The system of claim 10, wherein temperatures in the column are maintained within a range of about 35 to 75 degrees C.

12. The system of claim 11, wherein temperatures in the column are maintained within a range of about 45 to 65 degrees C.

13. The system of claim 1, wherein flow rates within the system are controlled for analysis.

14. The system of claim 13, wherein gas flow rates within the system are maintained within a range of about 75 to 200 cc/min.

15. The system of claim 14, wherein gas flow rates within the system are maintained within a range of about 100 to 150 cc/min.

16. The system of claim 13, wherein liquid flow rates within the system are maintained within a range of about 200-800 ml/min.

17. The system of claim 16, wherein liquid flow rates within the system are maintained within a range of about 300-500 ml/min.

18. The system of claim 1, wherein pressures within the system are controlled for analysis.

19. The system of claim 18, wherein pressures of the gas phase and liquid phase within the system are maintained within a range of about 5 to 50 psi.

20. The system of claim 19, wherein pressures of the gas phase and liquid phase within the system are maintained within a range of about 10 to 35 psi.

21. The system of claim 1, wherein the chemical analyzer comprises one or more spectrofluorometers.

22. The system of claim 1, wherein the chemical analyzer comprises one or more gas chromatographs.

23. The system of claim 1, wherein a proportionality constant is used to determine the concentration of the one or more solutes in the process stream.

24. The system of claim 23 wherein the proportionality constant is determined experimentally.

25. The system of claim 1, being configured to return the liquid phase to the process stream upon exiting the liquid outlet.

26. The system of claim 25, being configured to return at least a portion of the gas phase to the process stream upon exiting the flow cell.

27. The system of claim 25, wherein the carrier gas within the gas phase is vented or collected.

28. The system of claim 1 wherein the packing material is removable and interchangeable.

29. A method of continuously online compositional analysis of a process stream in an industrial process, the method comprising:

(a) continuously transporting, without trapping, a liquid phase of a process stream in a downstream direction through a fluid flow conduit extending from a liquid inlet to a liquid outlet, the fluid flow conduit including a chemically inert packed column (A/D column);

(b) continuously transporting a carrier gas into the A/D column through a gas inlet to contact the liquid phase within the A/D column across insert packing material;

(c) continuously producing a gas phase combination of the carrier gas and one or more solutes from the liquid phase exiting the A/D column at equilibrium with the liquid phase through the gas outlet;

(d) continuously transporting the gas phase exiting the A/D column to a flow cell communicably coupled to the gas outlet, the flow cell configured to transport the gas phase therethrough;

(e) with a chemical analyzer operatively engaged with the flow cell, capturing response to analysis of the gas phase in the flow cell;

(f) with the chemical analyzer, using the captured response to determine presence and concentration of the one or more solutes within the gas phase; and (g) with a processor communicably coupled to the analyzer, using the concentration of the one or more solutes within the gas phase to continuously perform a headspace analysis to determine the concentration of the one or more solutes in the process stream.

30. The method of claim 29, wherein said (e) and (f) further comprise: with a radiative analyzer operatively engaged with the flow cell, applying radiation to the gas phase in the flow cell, and capturing responsive radiation from the flow cell; and with the radiative analyzer, using the captured responsive radiation to determine presence and concentration of the one or more solutes within the gas phase.

* * * * *